US006709344B2

(12) United States Patent
Erickson et al.

(10) Patent No.: US 6,709,344 B2
(45) Date of Patent: *Mar. 23, 2004

(54) MEASUREMENT OF THE COEFFICIENT OF RESTITUTION OF A GOLF CLUB

(75) Inventors: Matthew J. Erickson, San Diego, CA (US); Pin Fan, Carlsbad, CA (US); Steven M. Ehlers, Poway, CA (US); John B. Kosmatka, Encinitas, CA (US)

(73) Assignee: Callaway Golf Company, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/249,197

(22) Filed: Mar. 21, 2003

(65) Prior Publication Data

US 2003/0144069 A1 Jul. 31, 2003

Related U.S. Application Data

(63) Continuation of application No. 09/844,160, filed on Apr. 27, 2001, now Pat. No. 6,585,605, which is a continuation-in-part of application No. 09/826,544, filed on Apr. 4, 2001, now Pat. No. 6,527,648.

(51) Int. Cl.[7] ............................................... A63B 53/00
(52) U.S. Cl. ....................................................... 473/282
(58) Field of Search ................................ 473/221, 282, 473/290, 291, 329, 342, 559, 351; 73/1.37, 1.38, 1.39, 54.23, 65.03, 78, 82, 570, 579, 659, 662, 778, 844

(56) References Cited

U.S. PATENT DOCUMENTS

| 4,870,868 | A | * | 10/1989 | Gastgeb et al. ................ 73/649 |
| 4,928,965 | A | * | 5/1990 | Yamaguchi et al. ......... 473/332 |
| 5,682,230 | A | | 10/1997 | Anfinsen et al. |
| 5,703,294 | A | * | 12/1997 | McConnell et al. ........... 73/579 |
| 5,803,832 | A | * | 9/1998 | Nakamura et al. ........... 473/377 |
| 6,165,081 | A | * | 12/2000 | Chou .......................... 473/329 |
| 6,289,735 | B1 | * | 9/2001 | Dister et al. .................. 73/579 |
| 6,354,962 | B1 | | 3/2002 | Galloway et al. |

OTHER PUBLICATIONS

Cochran, Alastair "Science and Golf III, Proceedings of the 1998 Wordl Scientific Congress of Golf", Human Kinetics (199.

* cited by examiner

Primary Examiner—Kim Nguyen
(74) Attorney, Agent, or Firm—Michael A. Catania; Elaine H. Lo

(57) ABSTRACT

A method (100) and system (20) for predicting a coefficient of restitution (COR) of a golf club (30) or golf club head (36) is disclosed herein. The system (20) and method (100) are able to predict the COR in a non-destructive manner for a particular golf ball and impact speed. The system (20) and method (100) utilize a vibration sensor (24) attached to the face (34) of a golf club (30). The vibration sensor (24) is excited with an excitation device (26), and data is transmitted to an analyzer (22). A mathematical model of the golf club (30) is created allowing for the coefficient of restitution to be predicted without destroying the golf club (30).

1 Claim, 10 Drawing Sheets

MEASUREMENT OF THE COEFFICIENT OF RESTITUTION OF A GOLF CLUB

CROSS REFERENCE TO RELATED APPLICATIONS

The present application is a continuation application of U.S. Pat. No. 6,585,605, which was filed on Apr. 27, 2001, which is a continuation-in-part application of U.S. patent application Ser. No. 09/826,544, which was filed on Apr. 4, 2001, now U.S. Pat. No. 6,527,648 filed on Mar. 4, 2003.

FEDERAL RESEARCH STATEMENT

[Not Applicable]

BACKGROUND OF INVENTION

1. Field of the Invention

The present invention relates to a system and method for measuring the coefficient of restitution of a golf club. More specifically, the present invention relates to an on-site system and method for measuring the coefficient of restitution of a golf club without alteration of the golf club.

2. Description of the Related Art

In 1998, the United States Golf Association ("USGA") decided to regulate technological improvements through a liberal interpretation of Rule 4.1 of the Rules of Golf, as set forth by the USGA and the Royals and Ancient Club of Saint Andrews. The USGA determined that a golf club head having a coefficient of restitution ("COR") greater than 0.83, on a scale of 0.00 to 1.00, would be non-conforming under the Rules of Golf as a club head having a spring-like effect.

In order to determine the COR of a golf club head, the USGA devised a laboratory test that necessitates the removal of the shaft of a golf club. The test is conducted at the USGA testing laboratory requiring that a golf club be submitted to the USGA for conformance. The un-shafted golf club head is placed on a pedestal without securing the club head to the pedestal. A PINNACLE® Gold two-piece golf ball is fired at the face of the club head at 160 feet per second. The club head is knocked-off the pedestal, and the COR is measured by the rebound of the golf ball. A grid is established on the club face using the scorelines and etched vertical lines, further destroying the club and creating further uncertainties. The procedure is repeated at random sites on the grid on the face of the golf club until the point with the highest COR is determined from the test. The outbound velocity of the golf ball after impact with the face is determined using a light gate systems such as described in U.S. Pat. No. 5,682,230. A more detailed explanation of the test is provided at www.usga.com.

It is obvious to anyone skilled in the art that such a test is inapplicable to on-course testing, and requires a specific laboratory with skilled technicians to perform the test. Further, the "cannon test" results in destruction of the club. Yet further, the test is conducted on an unshafted club head, completely ignoring the shaft and grip. What is needed is a test that can be performed on course, with consistent repeatability, and minimal operator error.

SUMMARY OF INVENTION

The present invention provides a solution to the problems associated with testing for COR using the method of the prior art. The present invention is able to accomplish this by providing a method and system that measures the COR of a golf club in a non-destructive manner, and without removal of the shaft.

One aspect of the present invention is a method for predicting the coefficient of restitution of a golf club. The method includes attaching a vibration sensor to a face of the golf club. Next, the attached vibration sensor is excited or impacted with an excitation or impact device to generate vibrations in the face. Next, the force of impact or the excitation from the device and the vibrations measured by the vibration sensor are transmitted to an analyzer to generate frequency domain data for the golf club. Next, the frequency domain data for the golf club is transformed into a transfer function for the golf club. Then, a golf ball model for a specific golf ball is inputted into the transfer function along with an impact speed in order to generate a predicted COR for the golf club at a specified impact speed with the specific golf ball.

Another aspect of the present invention is a system for predicting the coefficient of restitution of a golf club during impact at a specified speed with a specific golf ball. The system includes an accelerometer, an excitation or impact means, and a calculation means. The accelerometer is attached to a point on the face of the golf club. The accelerometer has means for measuring the vibration of the face. The means for exciting or impacting the face of the golf club in order to vibrate the face has means for measuring the force of excitation or impact with the face. The calculation means calculates the coefficient of restitution of the golf club from the vibration of the face, the force of impact or excitation with the face from the impacting or exciting means, an effective mass of the golf club and a mass of a golf ball.

Another aspect of the present invention is a system and method for predicting the coefficient of restitution of a golf club head during impact with a golf ball. The system and method is as described above, however, instead of an entire golf club, only the golf club head is utilized for predicting the COR.

Yet another aspect of the present invention is a method for predicting the coefficient of restitution of a golf club using time domain data. The method includes attaching a vibration sensor to a face of the golf club. Then, the attached vibration sensor is excited or impacted with an excitation or impact device to generate vibrations in the face. Next, the force of impact or excitation from the device and the vibrations measured by the vibration sensor are transmitted to an analyzer to generate time domain data for the golf club. Next, the time domain data for the golf club is transformed into a state-space representation of the golf club. Then, a golf ball model for a specific golf ball is inputted into the state-space representation and an impact speed in order to generate a predicted COR for the golf club at a specified impact speed with the specific golf ball.

It is a primary object of the present invention to provide a method and apparatus for predicting the COR of a golf club or golf club head.

It is an additional object of the present invention to provide a method and apparatus for predicting the COR of a golf club in a non-destructive manner.

It is an additional object of the present invention to provide a method and apparatus for predicting the COR of a golf club that is portable, and may be performed on-course.

It is an additional object of the present invention to provide a method and apparatus for predicting the COR of a golf club that requires less time than the USGA cannon test.

Having briefly described the present invention, the above and further objects, features and advantages thereof will be recognized by those skilled in the pertinent art from the following detailed description of the invention when taken in conjunction with the accompanying drawings.

DETAILED DESCRIPTION

The present invention is directed at a method and system for measuring the coefficient of restitution (also referred to herein as "COR") of a golf club in a non-destructive manner. The COR is generally set forth by the following equation:

$$e = \frac{v_2 - v_1}{U_1 - U_2}$$

wherein $U_1$ is the club head velocity prior to impact; $U_2$ is the golf ball velocity prior to impact which is zero; $v_1$ is the club head velocity just after separation of the golf ball from the face of the club head; $v_2$ is the golf ball velocity just after separation of the golf ball from the face of the club head; and e is the coefficient of restitution between the golf ball and the club face. The values of e are limited between zero and 1.0 for systems with no energy addition. The coefficient of restitution, e, for a material such as a soft clay or putty would be near zero, while for a perfectly elastic material, where no energy is lost as a result of deformation, the value of e would be 1.0.

Figure 1:
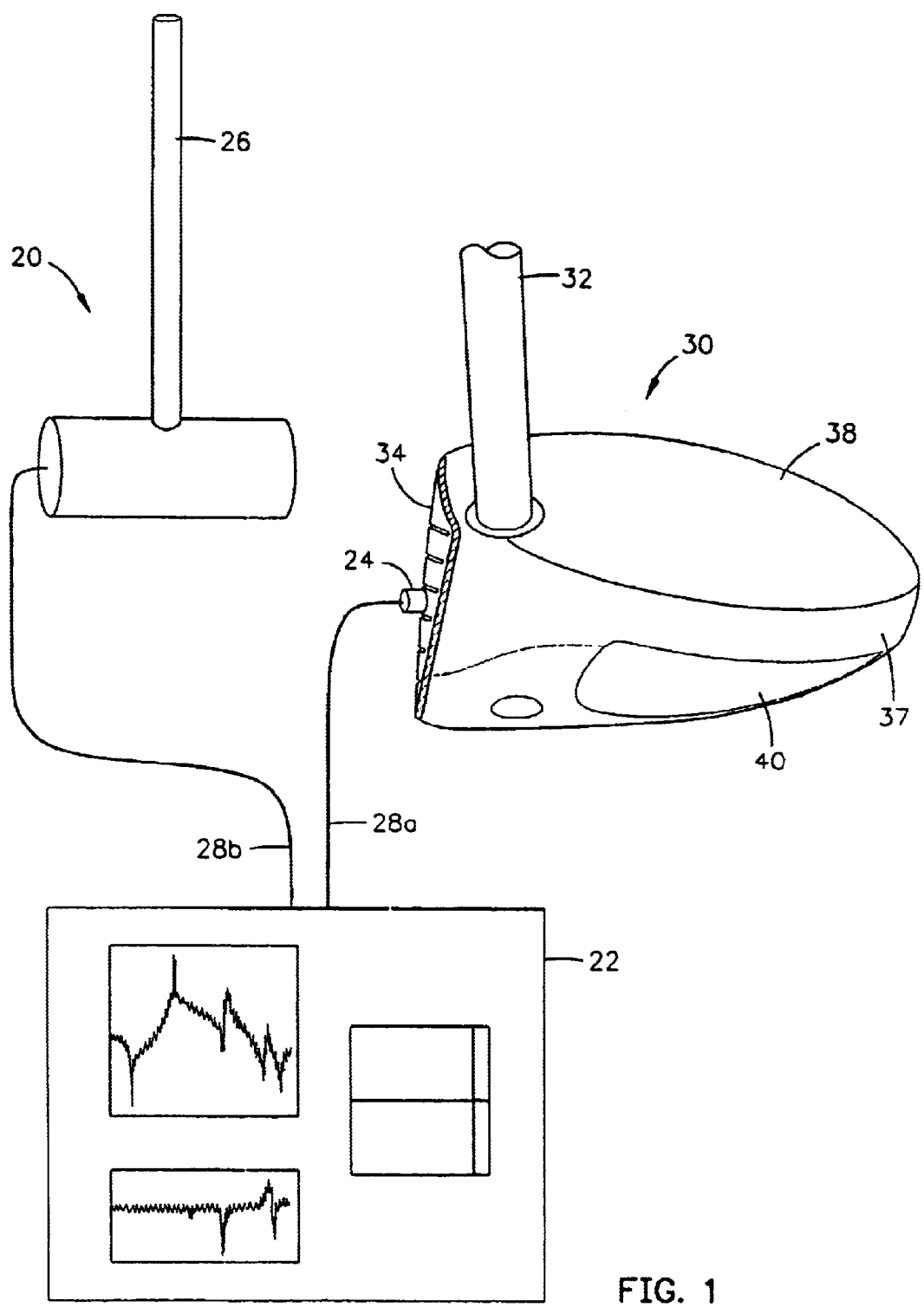
FIG. 1 is a schematic view of the system of the present invention.
Figure 2:
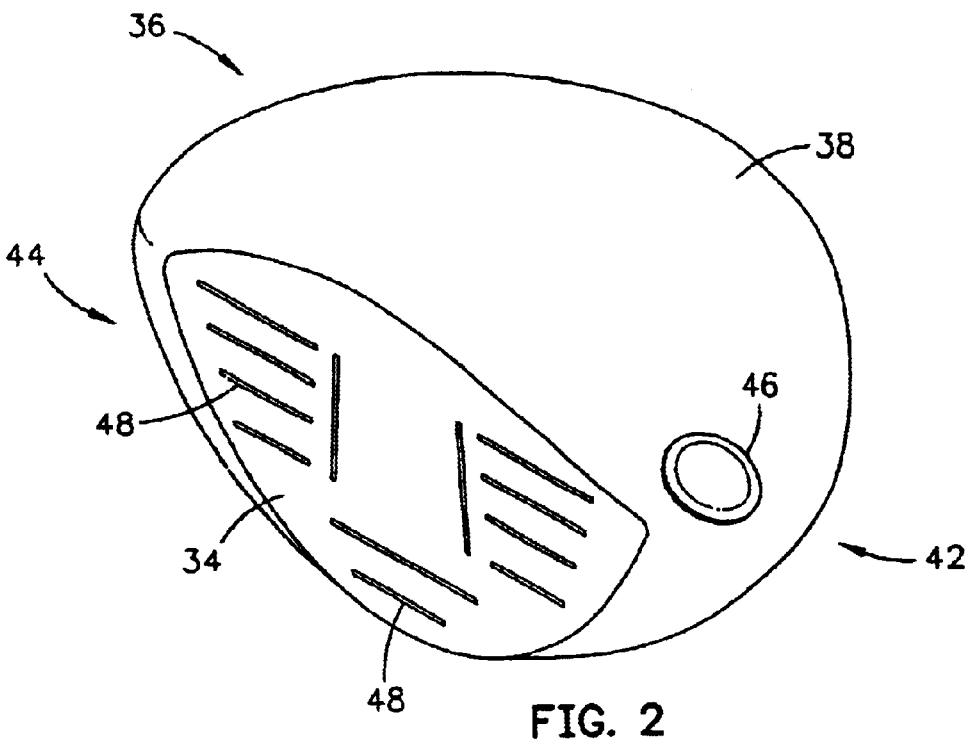
FIG. 2 is a perspective view of a golf club head.
Figure 3:
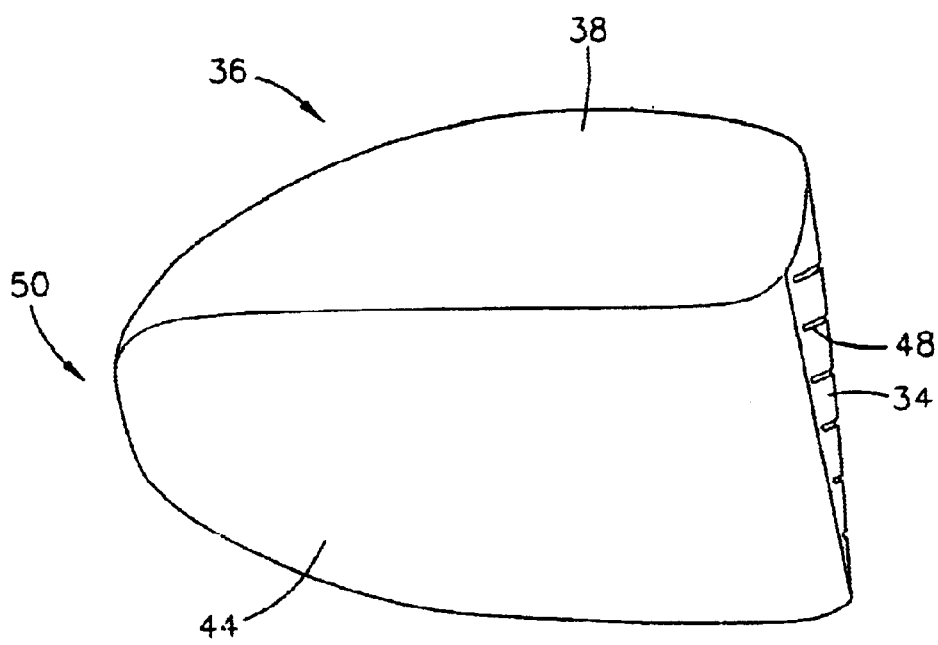
FIG. 3 is a toe end side view of the golf club head of FIG. 2.
Figure 4:
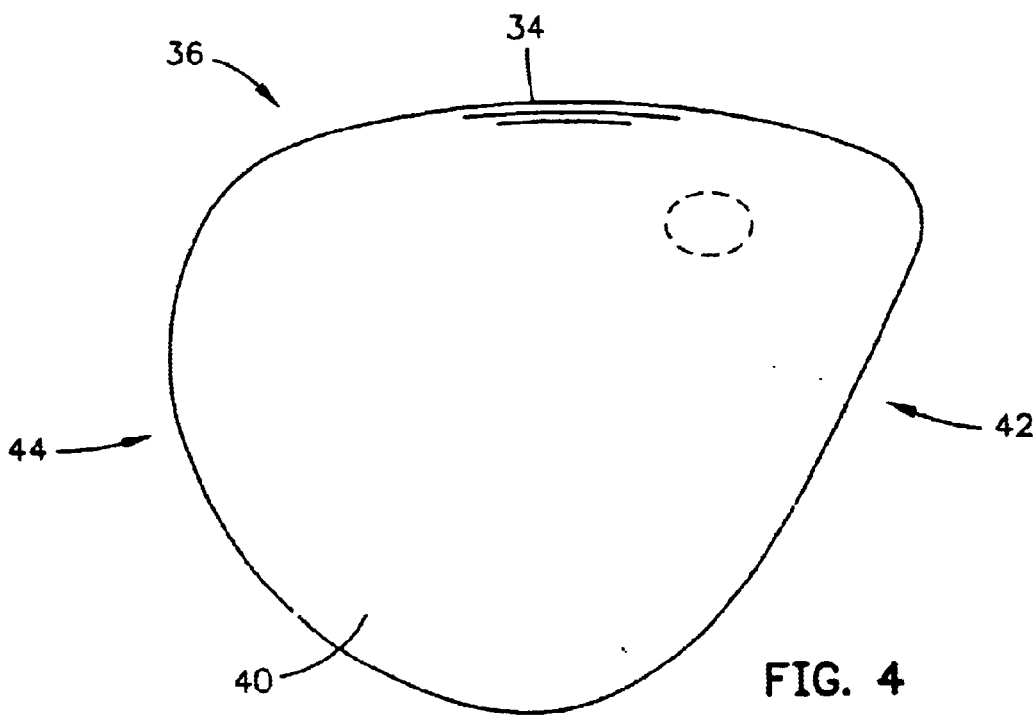
FIG. 4 is a bottom view of the golf club head of FIG. 2.
Figure 5:
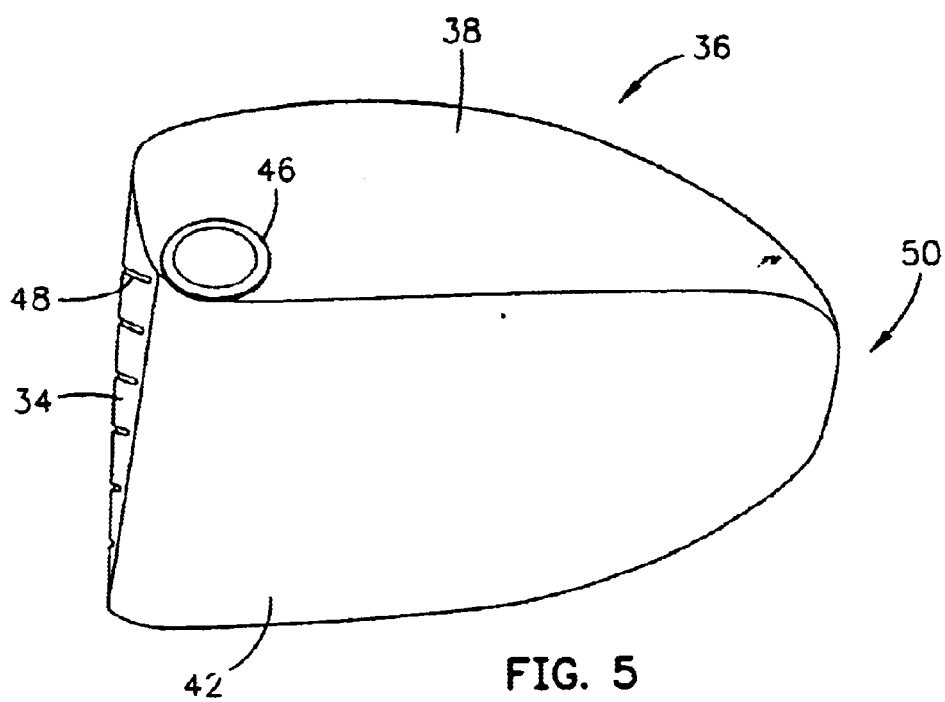
FIG. 5 is a heel end side view of the golf club head of FIG. 2.

As shown in FIG. 1, the system of the present invention is generally designated 20. The system includes an analyzer 22, a vibration sensor 24 and an impact device 26. The vibration sensor 24 and the impact device 26 are preferably connected to the analyzer through wires 28a and 28b. However, those skilled in the art will recognize that other data transmission means, such as wireless transmission, could be used without departing from the scope and spirit of the present invention.

The vibration sensor 26 is attached to a golf club 30 through use of an adhesive 29 such as epoxy, beeswax, or the like. As shown in FIGS. 1–5, the golf club 30 includes a shaft 32, a face 34, a golf club head 36 with a body 37. The body 37 of the club head 36 generally includes the face 34, a crown 38 and a sole 40. The club head 36 is partitioned into a heel section 42 nearest the shaft 32, a toe section 44 opposite the heel section 42, and a rear section 50 opposite the face 34. The face 34 has a plurality of scorelines 48 thereon. The club head 36 has a hosel 46 for receiving the shaft 32, and the hosel 46 may be internal or external.

Figure 6:
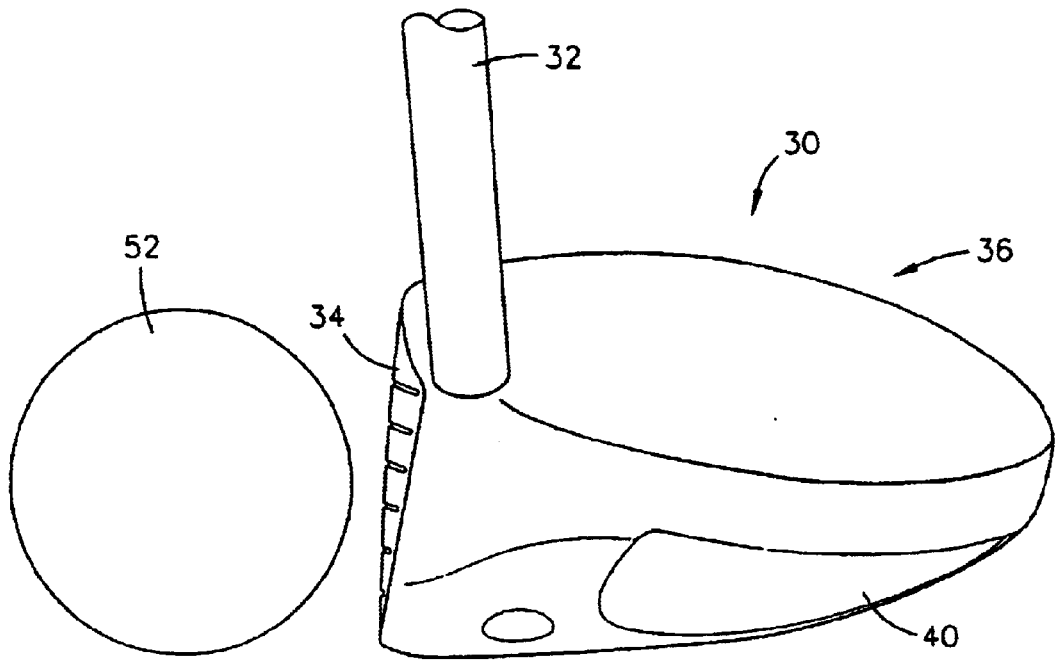
FIG. 6 is a side view of a golf club prior to impact with a golf ball.
Figure 7:
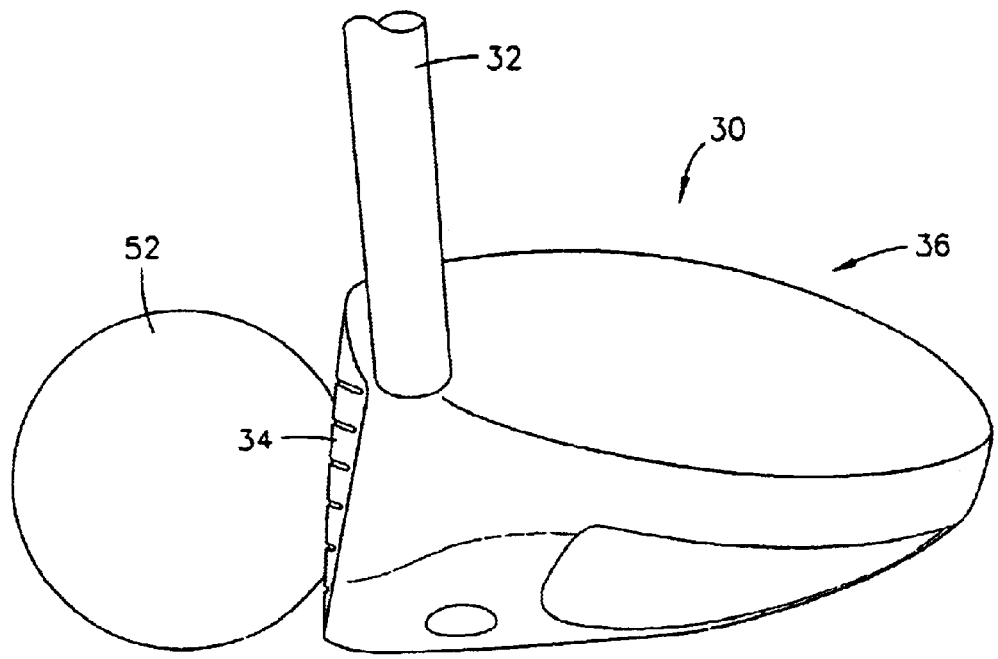
FIG. 7 is a side view of a golf club during impact with a golf ball.
Figure 8:
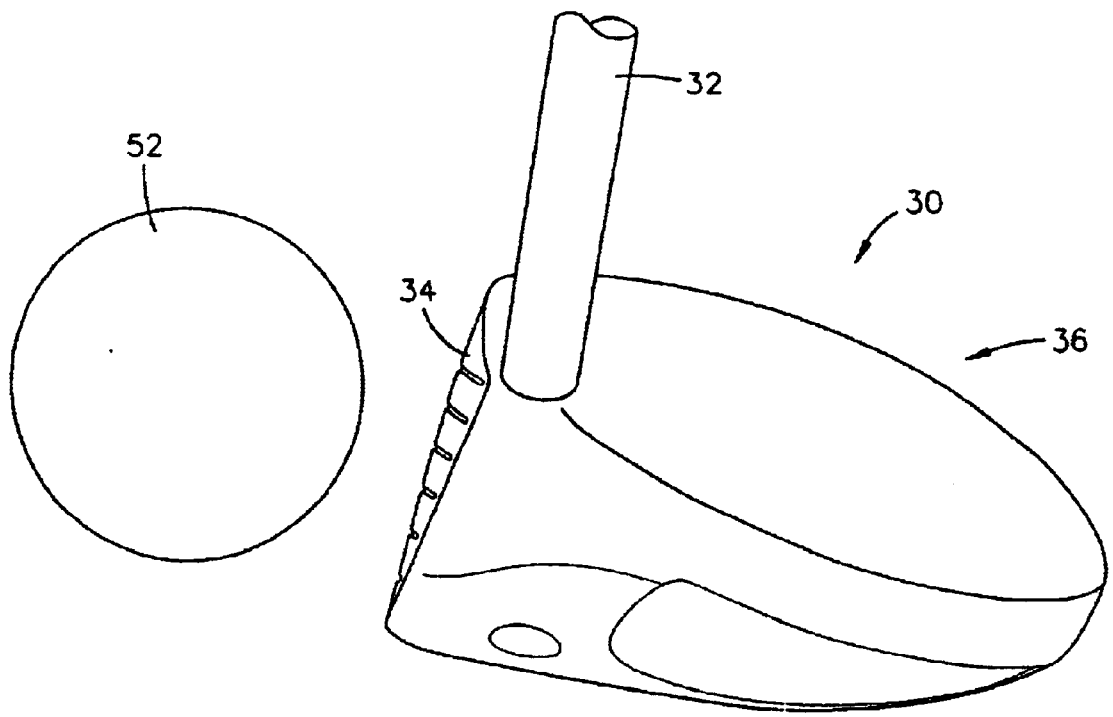
FIG. 8 is a side view of a golf club after impact with a golf ball.

The club head 36 is typically composed of a stainless steel material or a titanium material. However, those skilled in the art will recognize that the club head 36 may be composed of other materials such as vitreous metals, ceramics, composites, carbon, carbon fibers and other fibrous materials. The club head 36 is typically cast or forged, and the thickness of the crown 38, the sole 40 and the face 34 may be constant or varying. Typically, the construction of the face 34 will effect the COR of the golf club. For example, a high COR golf club is disclosed in U.S. Pat. No. 6,354,962, filed on Nov. 1, 1999, entitled Golf Club Head With Face Composed of a Forged Material, which pertinent parts are hereby incorporated by reference. An example of a low COR golf club would be a golf club head composed of a persimmon wood. As shown in FIGS. 6–8, the flexibility of the face 34 allows for a greater coefficient of restitution. At FIG. 6, the face 34 is immediately prior to striking a golf ball 52. At FIG. 7, the face 34 is engaging the golf ball 52, and deformation of the golf ball 52 and face 34 is illustrated. At FIG. 8, the golf ball 52 has just been launched from the face 34.

In a preferred embodiment, the vibration sensor 24 is an accelerometer that is capable of measuring the vibrations of the face 34 generated by impact with an impact device 26. An alternative vibration sensor 24 is a laser Doppler vibrometer. The accelerometer may have a titanium cap for protection during impact. The impact device 26 is preferably a hammer with a connection to measure the force in volts, and transmit the force information to the analyzer 22 via the wire 28b. An alternative impact device 26 is a fixed striking device that would remove any operator error. In an alternative embodiment, the impact device is an excitation device that imparts vibrations in the face 34. However, those skilled in the pertinent art will recognize that other impact or excitation devices 26 may be used without departing from the scope and spirit of the present invention. The analyzer 22 is preferably a spectrum analyzer such as an OROS-OR763 spectrum analyzer available from OROS S.A. of France.

Figure 9:
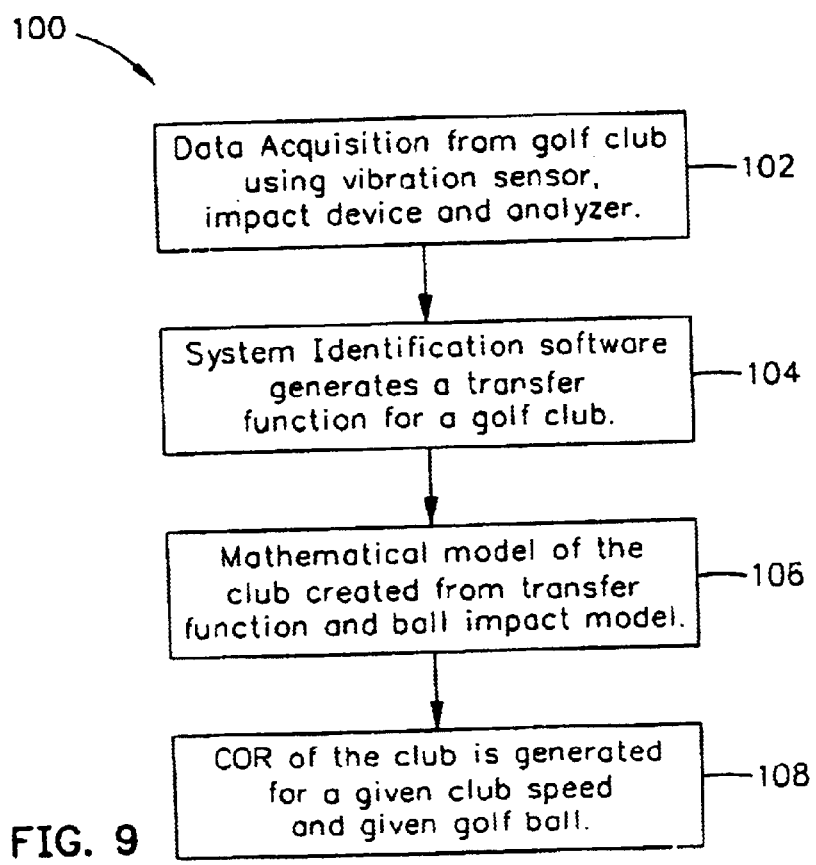
FIG. 9 is a flow chart of the general method of the present invention.

The general method is set forth in FIG. 9, which is a flow chart of the overall method 100. At block 102, the information is acquired from the golf club 30 by the system 20, as described in greater detail below. At block 104, the acquired data is transformed into a transfer function using a software such as MATLAB frequency domain system identification toolbox, as described in greater detail below. At block 106, the transfer function is utilized with additional information to create a mathematical model of the club. At block 108, either of the following equations is utilized to generate the COR of the club 30 for a given golf ball 52 at a predetermined impact speed:

$$COR = (V'_{ball}/V_{club})(1+m_{ball}/M_{effective\ club}) - 1$$

$$COR = (-V'_{ball}/V_{ball})(1+m_{ball}/m_{effective\ club}) + m_{ball}/m_{effective\ club}$$

Figure 10:
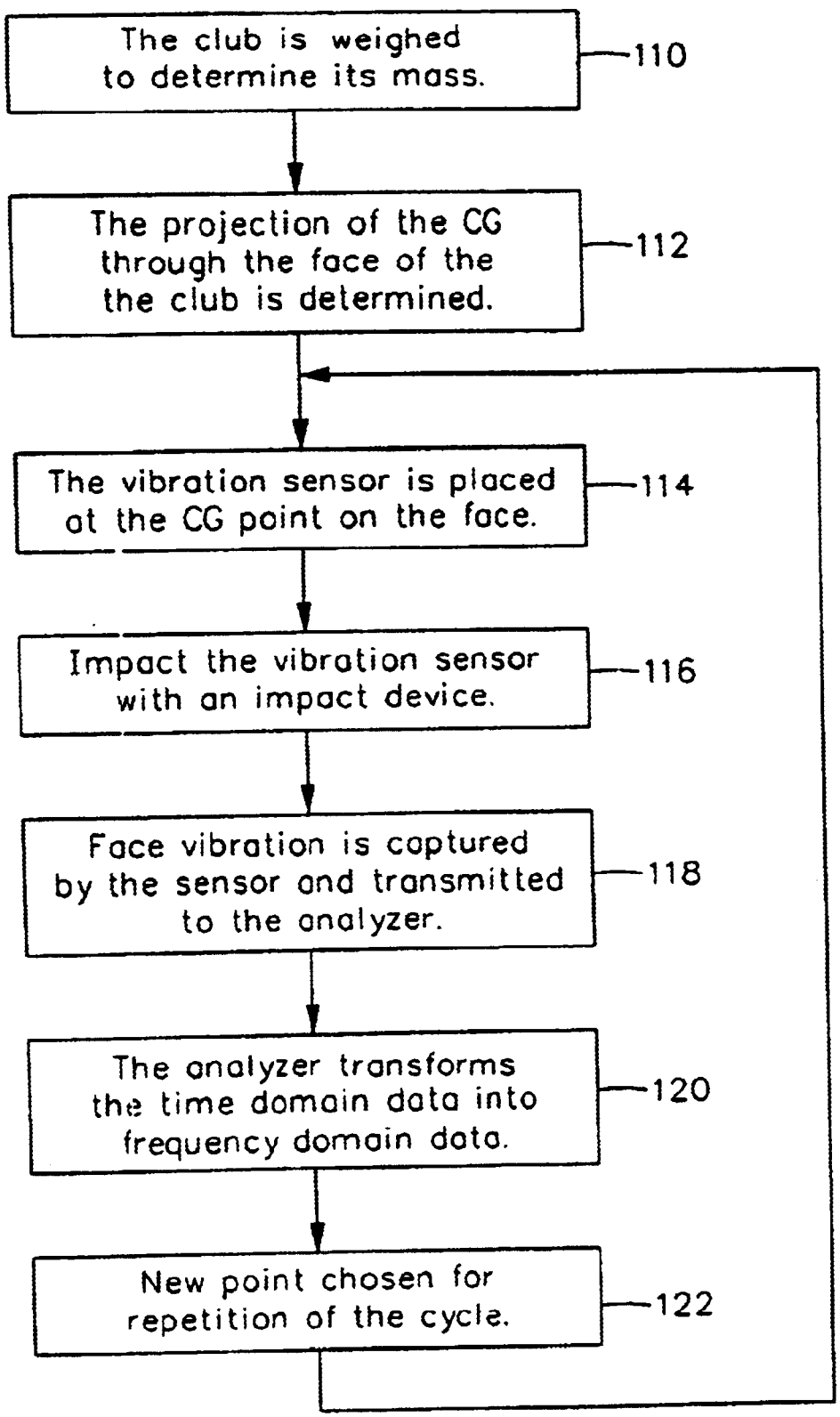
FIG. 10 is a flow chart of the data acquisition process of the method of the present invention.

$V_{ball}$ is the velocity of the golf ball after impact with the club. $V''_{ball}$ is the velocity of the golf ball if it is fired at the golf club instead of having the golf club swing at a stationary golf ball. $V_{club}$ is the swing speed of the club. $m_{ball}$ is the mass of the golf ball. $m_{effective\ club}$ is the effective mass of the golf club determined at zero frequency. The data acquisition process, block 102 of FIG. 9, is further explained in the flow chart of the FIG. 10. At block 110, the club 30 is weighed to obtain the mass of the club 30. At block 112, the projection of the center of gravity ("CG") through the face 34 is determined by using known methods of finding the CG, including laying the club face down on a flat surface. At block 114, the vibration sensor 24 is placed on the face 34 at the point where the CG projects through the face 34. As mentioned above, the sensor 24 may be mounted using beeswax, epoxy, or the like. It is preferred that an adhesive material with minimal insulating properties be used for mounting the vibration sensor 24 in order to allow the vibration sensor 24 to capture as true vibration as possible for the face 34. At block 116, the vibration sensor 24 is impacted/struck with the impact device 26, and the impact force, as measured in voltage, is transmitted by the impact device 26 to the analyzer 22 via the cable 28b. At block 118, a vibration is generated in the face 34 and this vibration is transmitted by the sensor 24 to the analyzer 22 via the cable 28a. At block 120, the analyzer 22 transforms the time domain data into a frequency domain equivalent. The output/input ratio (acceleration as indicated by vibration of the face 34/the impact force of the hammer 26) is generated by the analyzer 22 in a frequency domain. The frequency domain represents how the system 20 reacts at the location of the vibration sensor 24 to a unit impulse input into the system 20 at the location of the input force by the impact device 26. This impulse response indicates how the club 30 responds to a predetermined force such as impact with a golf ball 52. Those skilled in the art will recognize that time domain data could be substituted for the frequency domain data. At block 122, a new point may be chosen on the face 34 for placement of the vibration sensor 24 thereto. Then, at block 116, the sensor 24 is impacted with the impact device 26 and the cycle is repeated. The cycle may be repeated a multitude of times in order to obtain a grid of the face 34 showing the impulse response for different points on the face 34. Eventually, this grid information could be utilized to obtain the point on the face 34 with the highest COR.

Figure 11:
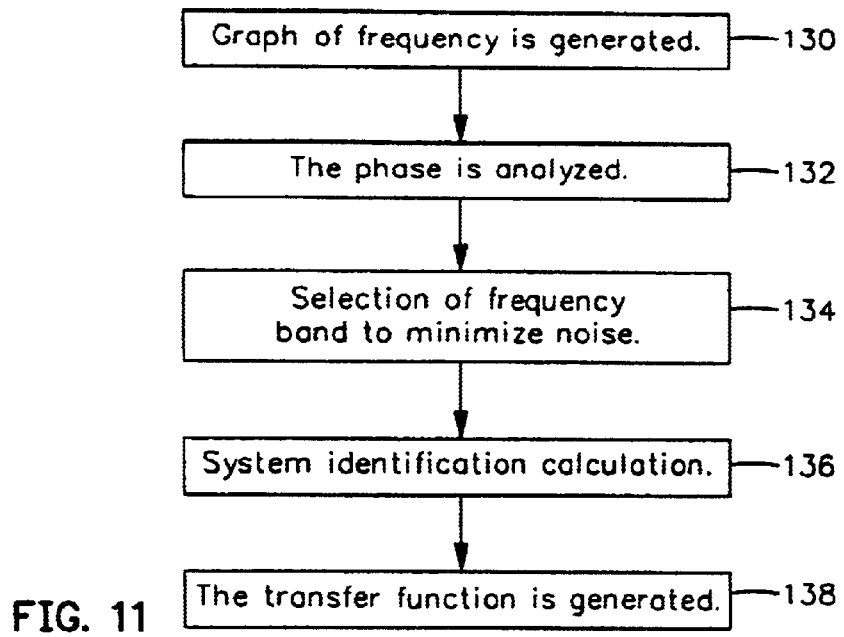
FIG. 11 is a flowchart of the transformation of the frequency domain data into a transfer function.

The transformation of the frequency domain data into a transfer function, block 104 of FIG. 9, is further explained in the flow chart of the FIG. 11. This transformation is preferably performed using the system identification software. System identification is a means for determining a model of a physical system. A model that is used for identifying models for dynamic physical systems is an ordinary differential equation or difference equation with constant coefficients. Linear dynamic systems can be described in two regimes: frequency and time. The frequency domain is preferred due to the proliferation of the digital computer and the fast Fourier transform. The general model used to identify dynamic linear systems in the frequency domain is set in FIG. 12. The transfer function $H(\Omega)$ represents the club 30 where '106 $=s=j\omega=j2\pi f$. "f" is the frequency and "j" is an imaginary number square root of negative one. "$\omega$" is the angular frequency. Xm and Ym represent the measured input and output complex amplitudes respectively. These values are the combination of noise (Nx and Ny) superimposed upon the theoretical true input and output amplitudes X and Y. The transfer function, in its rational fraction form, is as follows:

$$H(\Omega) = e^{-j\omega T_d} \frac{b_0\Omega^0 + b_1\Omega^1 + \ldots b_{nn}\Omega^{nn}}{a_0\Omega^0 + a_1\Omega^1 + \ldots a_{nd}\Omega^{nd}}$$

Advanced curve-fitting and cost function optimization is utilized to derive rational fraction polynomial numerator and denominator coefficients ($b_n$ and $a_n$) in the equation above. These coefficients are then used to form a theoretical transfer function that best represents the true model Y/X. This is then used to find the best fit to a measured transfer function that represents the physical system.

Figure 13:
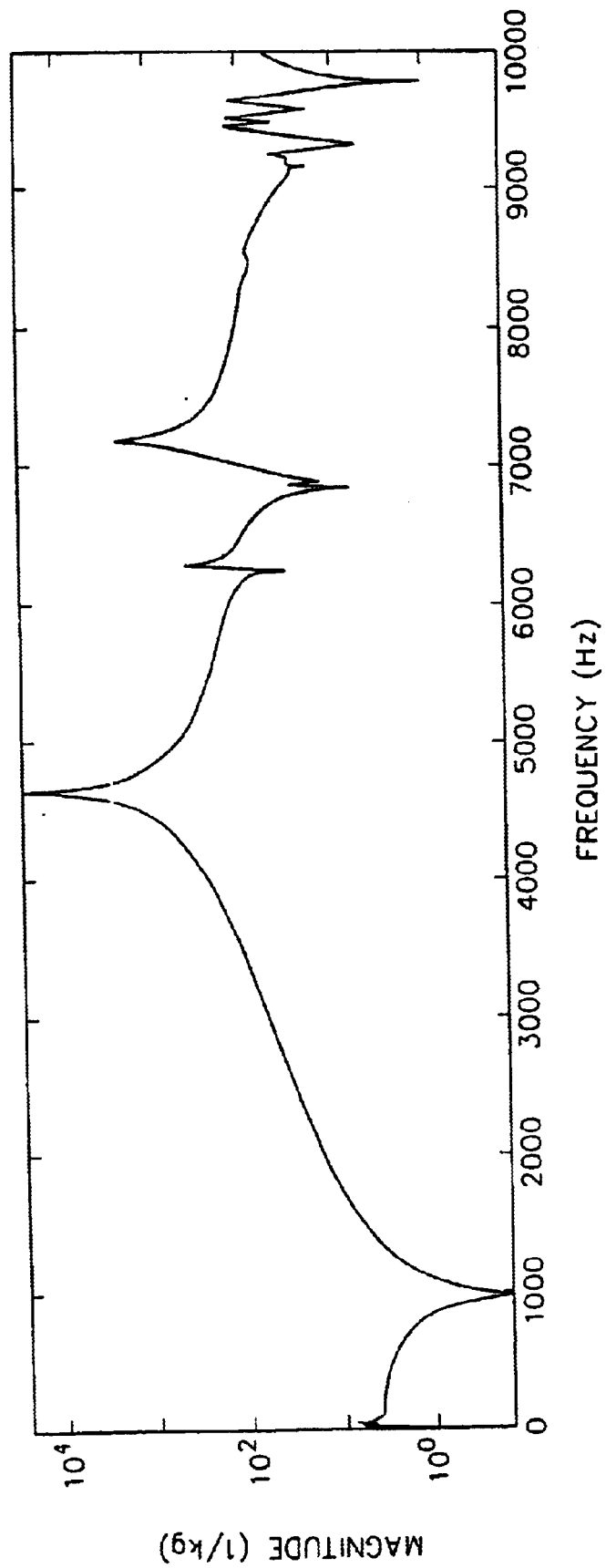
FIG. 13 is a graph of frequency versus magnitude of the fitted curve from the frequency domain data.

Referring again to FIG. 11, at block 130, a graph of frequency versus magnitude of transfer accelerance (1/kg) is generated from the frequency domain data, which is shown in FIG. 13. At block 132, the phase is analyzed to determine when the face 34 is traveling inward and outward. At block 134, a frequency band that is the best mathematical representation of the club 30 and minimizes noise is selected from the graph. The graph is analyzed to find the first and largest magnitude peak 131, which is the first vibration of the face 34. The graph is also analyzed to find the first anti-resonance 133, which is similar to an energy sink. The first inflection point 135 is also determined from the graph. Due to vibrations at higher frequencies which correspond to the crown 38, the sole, the face 34 or any combination thereof, the best mathematical representation of the club 30 is the information from 500 Hertz (Hz) to the first inflection point 135. At block 136, the system identification calculation is performed by the software. At block 138, the transfer function is generated from the fitted information from the graph.

Figure 12:
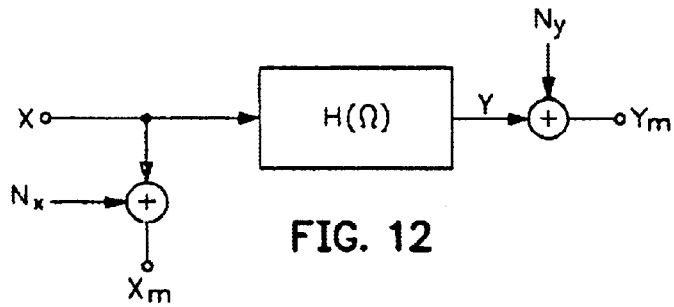
FIG. 12 is schematic diagram of the general model used to identify dynamic linear systems in the frequency domain.

In FIG. 12, the effective mass of the club 30 can be obtained at zero frequency since according to Newton's Second Law, Force= mass× acceleration, (F=ma) and 1/m= a/F. The effective mass is compared to the measured mass of the club.

It should be noted that the COR of a golf club 30 is dependent on the golf ball and speed of impact, and thus, the COR of a golf club will vary if the golf ball is changed or if the speed is changed. For example, if the COR is measured for a golf club 30 using a CALLAWAY GOLF® RULE 35® SOFTFEEL™ golf ball at a speed of 110 miles per hour ("mph"), the COR will be different than that measured using a CALLAWAY GOLF® CB1™ golf ball at a speed of 110 mph. Additionally, if the COR is measured for a golf club 30 using a CALLAWAY GOLF® RULE 35® SOFTFEEL™ golf ball at a speed of 110 mph, the COR will be different than that measured using a CALLAWAY GOLF® RULE 35® SOFTFEEL™ golf ball at a speed of 85 mph.

In order for the method and system 20 of the present invention to operate in a non-destructive manner, at block 106 of FIG. 9, a golf ball model must be used with the transfer function in order to have a means for generating the COR for a golf club 30. Just like the transfer function is unique to a specific golf club 30, the golf ball model is unique to a specific golf ball. Thus, the golf ball model for the a CALLAWAY GOLF® RULE 35® SOFTFEEL™ golf ball (a three-piece solid golf ball with a very thin thermoset polyurethane cover) is different than a CALLAWAY GOLF® CB1™ golf ball (a two-piece golf ball with an ionomer blend cover). The golf ball model is obtained by recording: the inbound speed and outbound speed for a specific golf ball fired at a zero degree loft striking plate; the contact duration; the contact force; and the COR of the golf ball. This data is obtained for different speeds and a nonlinear ball model is created such as disclosed in Chapter 61 of Alastair Cochran's *Science and Golf III, Proceedings of the* 1998 *World Scientific Congress of Golf*, Human Kinetics 1999.

Figure 14:
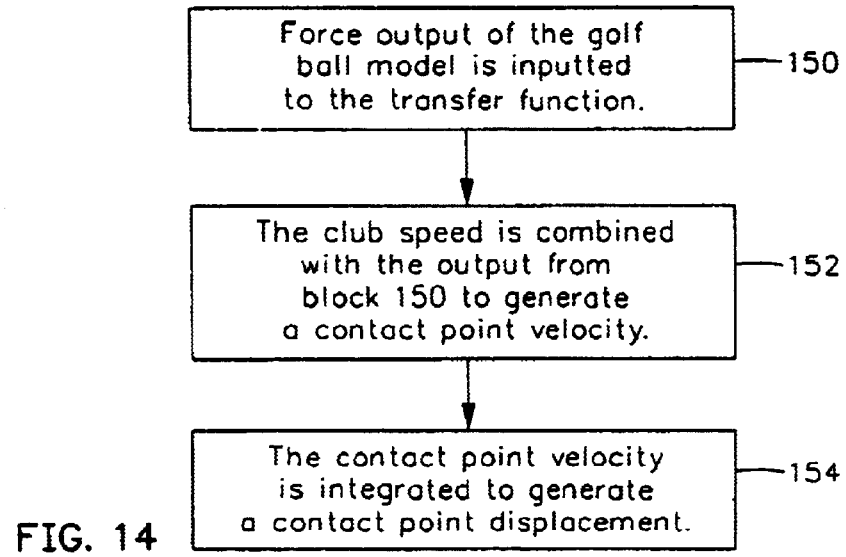
FIG. 14 is a flow chart of the ball model input into the transfer function.

As shown in the flow chart of FIG. 14, at block 150, the force output of the golf ball model is inputted to the transfer function. At block 152, the club speed with the output from block 150 generates a contact point velocity. At block 154, the contact point velocity is integrated to give the contact point displacement, which is a representation of the bending of the face 34 about the golf ball 52.

This information is used in block 108 of FIG. 9 to input into the previously mentioned equations to obtain the COR:

$$COR = (V_{ball}/V_{club})(1 + m_{ball}/m_{effective\ club}) - 1$$

$$COR = (-V_{ball}/V_{ball})(1 + m_{ball}/m_{effective\ club}) + M_{ball}/M_{effective\ club}$$

For example, a CALLAWAY GOLF® HAWK EYE® nine degree driver (club head only) was tested using the present invention. The driver had a measured mass of 195.9 grams and an effective mass of 193.9 grams. Using a contact point velocity of 21.9 feet per second, and a $V_{out}/V_{in}$ ratio of 0.4485, the COR was predicted to be 0.7905.

Figure 15:
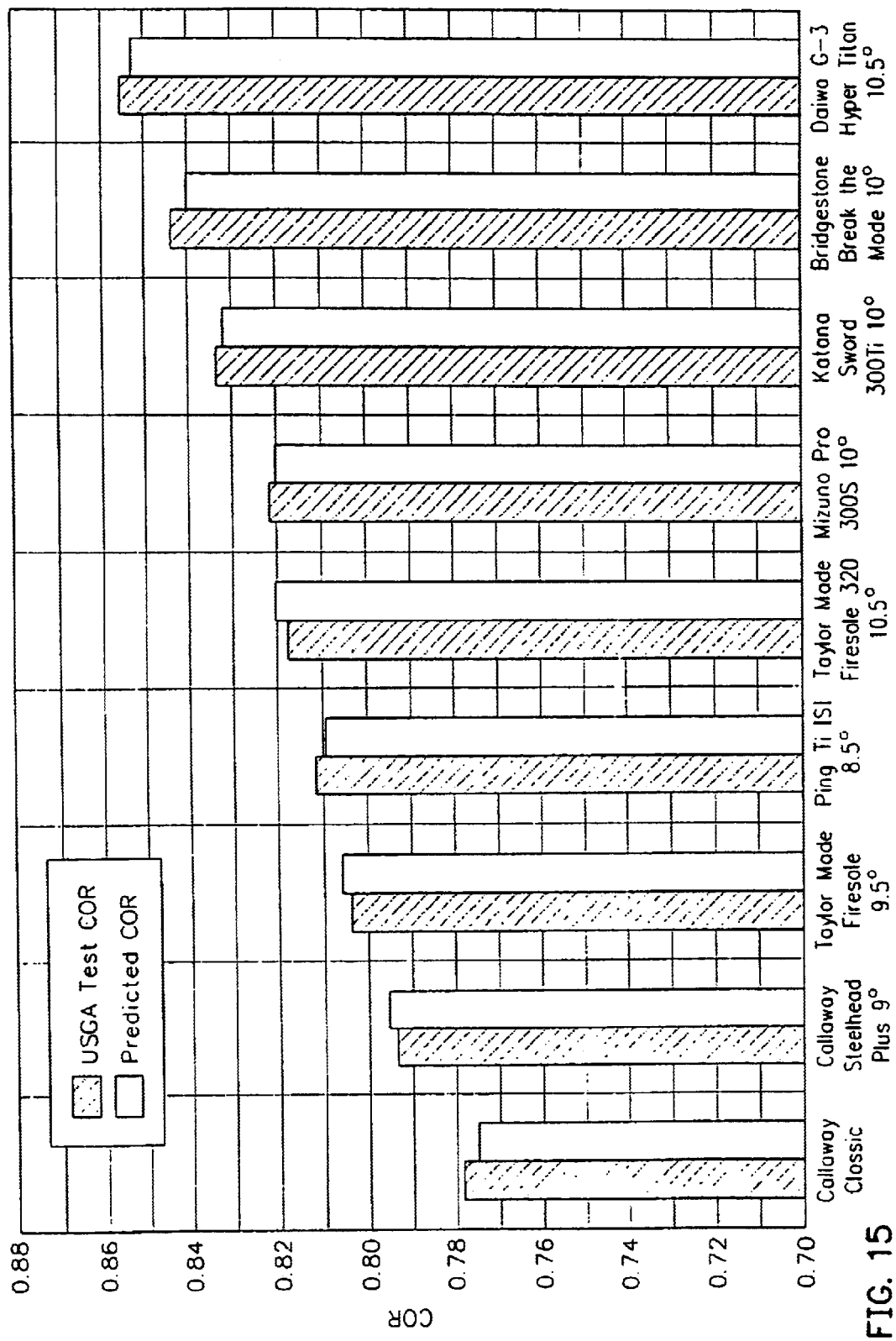
FIG. 15 is a chart comparing the predicted values of several golf clubs using the present invention versus the USGA cannon test values.
Figure 16:
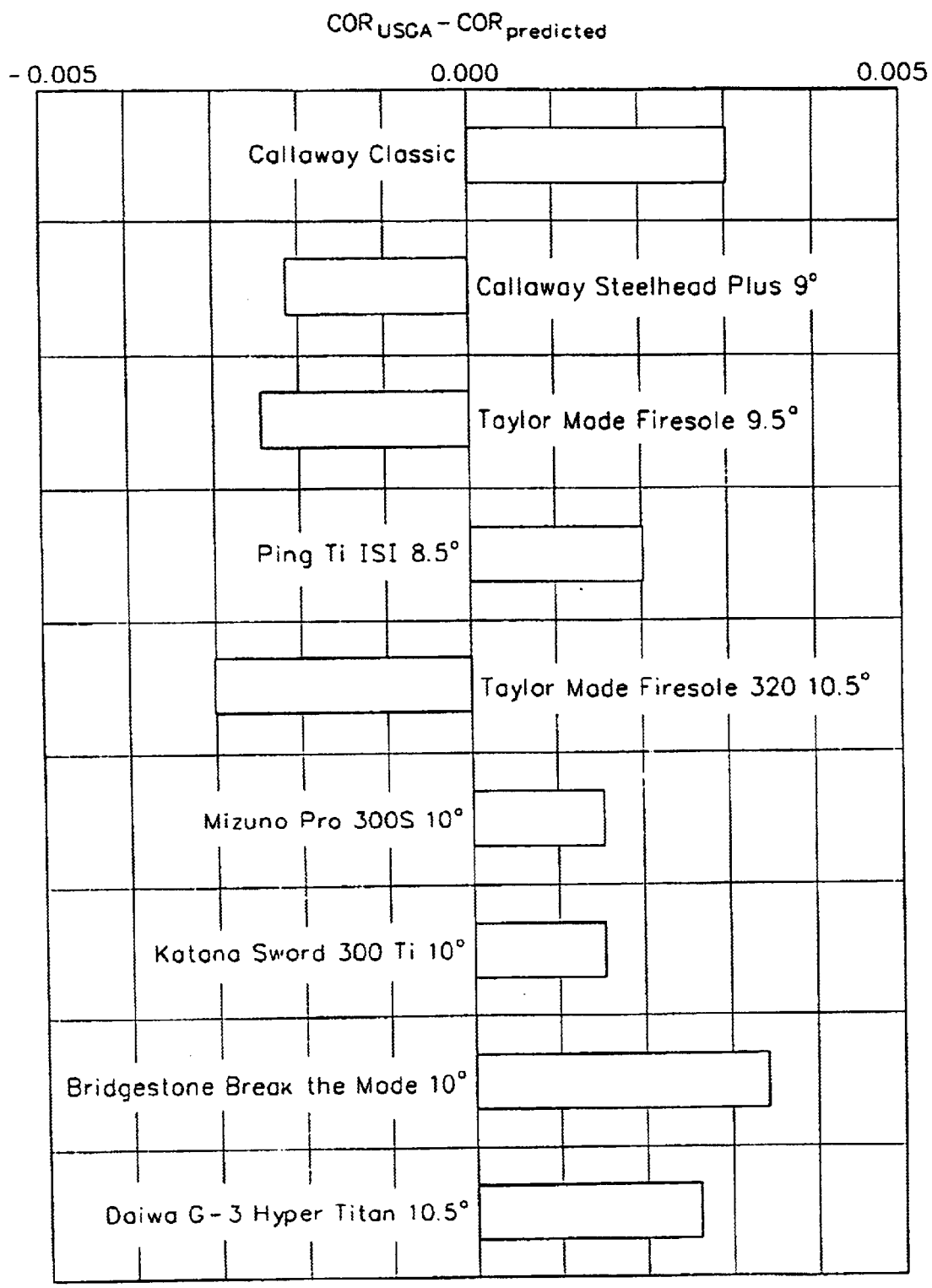
FIG. 16 is a chart demonstrating the differences in values between the present invention and the USGA cannon test for the golf clubs in the chart of FIG. 15.

FIG. 15 illustrates a chart of the COR values generated from the method and system of the present invention as compared to the COR values generated from the USGA cannon test as previously described and as set forth on the USGA web site. The nine club heads are composed of titanium, titanium alloy, stainless steel, or in the case of the CALLAWAY® CLASSIC® golf club, persimmon wood. FIG. 16 illustrates the difference in values between the method and system of the present invention and the USGA cannon test for the nine clubs. The actual numbers are provided in Table One below. As mentioned above, the present invention may be utilized for clubs or for club heads. In order to provide a more accurate comparison to the USGA test, the information in FIGS. 15 and 16, and in Table One is for club heads. As is apparent from FIG. 16, the predicted COR from the present invention is within ±0.008 of the USGA values.

| Club Head | Ball mass | Head mass | Predicted COR | USGA COR |
|---|---|---|---|---|
| Callaway Classic | 0.0456 | 0.19813 | 0.775 | 0.778 |
| Callaway Steelhead Plus 9° | 0.0456 | 0.20106 | 0.795 | 0.793 |
| Taylor Made Firesole 9.5° | 0.0456 | 0.20377 | 0.805 | 0.803 |
| PING Ti ISI 8.5° | 0.0456 | 0.19974 | 0.809 | 0.811 |
| Taylor Made Firesole 320 10.5° | 0.0456 | 0.18855 | 0.820 | 0.817 |
| Mizuno Pro 300 S 10° | 0.0456 | 0.19998 | 0.820 | 0.821 |
| Katana Sword 300 Ti 10° | 0.0456 | 0.1924 | 0.832 | 0.833 |
| Bridgestone Break the Mode 10° | 0.0456 | 0.19672 | 0.840 | 0.843 |
| Daiwa G-3 Hyper Titan 10.5° | 0.0456 | 0.18781 | 0.852 | 0.855 |

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims.

We claim as our invention:

1. A system for predicting a coefficient of restitution (COR) of a golf club head, the system comprising:

an accelerometer for measuring vibrations of a face of the golf club head;

an impact device to impact the face of a golf club head and generate vibrations in the face of the golf club head;

means for transmitting to an analyzer a force of impact from the impact device during impact with the face of a golf club head, and the vibrations of the face measured by the accelerometer, the analyzer generating frequency domain data for the golf club head from the force of impact and vibrations;

means for generating a graph of frequency versus magnitude of transfer accelerance from the frequency domain data;

means for selecting a frequency band to minimize noise, the frequency band ranging from 500 Hertz to a first inflection point of the graph;

means for calculating a transfer function from the frequency band of the graph; and means for predicting a COR for the golf club head at an impact speed with a golf ball by inputting a golf ball model for a specific golf ball and an impact speed into the transfer function that contains an acceleration magnitude and direction of the face of the golf club in order to generate a predicted COR for the golf club head at the impact speed with the specific golf ball, the golf ball model comprising a contact duration of the specific ball, a contact force of the specific ball, a COR of the specific ball and a mass of the specific ball.

* * * * *